(12) United States Patent
Gan et al.

(10) Patent No.: US 7,074,867 B2
(45) Date of Patent: Jul. 11, 2006

(54) ION CONDUCTING POLYMERS

(75) Inventors: Leong Ming Gan, Singapore (SG); Pei Yong Chow, Singapore (SG)

(73) Assignee: Agency for Science, Technology and Research, Centros (SG)

( * ) Notice: Subject to any disclaimer, the term of this patent is extended or adjusted under 35 U.S.C. 154(b) by 209 days.

(21) Appl. No.: 10/719,667

(22) Filed: Nov. 21, 2003

(65) Prior Publication Data

US 2004/0171781 A1 Sep. 2, 2004

Related U.S. Application Data

(63) Continuation-in-part of application No. 10/176,958, filed on Jun. 21, 2002, now abandoned.

(30) Foreign Application Priority Data

Jun. 25, 2001 (SG) .............................. 200103843-9

(51) Int. Cl.
*C08F 118/02* (2006.01)
*C08D 249/08* (2006.01)

(52) U.S. Cl. ...................... 526/319; 526/915; 544/224; 544/336; 548/267.8; 548/341.1; 548/376.1; 548/252

(58) Field of Classification Search ................ 526/319, 526/915; 544/224, 336; 548/267.8, 341.1, 548/376.1, 252
See application file for complete search history.

(56) References Cited

U.S. PATENT DOCUMENTS 4,681,912 A 7/1987 Durand et al.
5,151,217 A 9/1992 Price
5,521,229 A 5/1996 Lu et al.
5,895,799 A 4/1999 Wu et al.

FOREIGN PATENT DOCUMENTS

| EP | 100530 | 2/1984 |
|---|---|---|
| EP | 531005 | 3/1993 |
| JP | 2001-294706 | 10/2001 |
| WO | WO 95/34583 | 12/1995 |
| WO | WO 99/27599 | 6/1999 |
| WO | WO 00/51198 | 8/2000 |
| WO | WO 00/52060 | 9/2000 |
| WO | WO 00/66652 | 11/2000 |
| WO | WO 02/22712 | 3/2002 |

OTHER PUBLICATIONS

Kuo, et al., "Photoinitiated polymerization of styrene in microemulsions," Macromolecules (1987) 20:1216-1221.
Peled, et al., "A novel proton conductivity membrane (PCM)," J. Electrochem. Soild State Lett. (1998) 1:210-211.

*Primary Examiner*—Robert D. Harlan
(74) *Attorney, Agent, or Firm*—Carol A. Schneider; Mintz, Levin, Cohn, Ferris Glovsky and Popeo, P.C.

(57) ABSTRACT

A compound having the general formula (I):

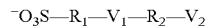

wherein $R_1$ is a hydrocarbon radical comprising $C_1$ to $C_{10}$ main chain carbon atoms, wherein hydrogen atoms bonded to the main chain carbon atoms are optionally substituted; $R_2$ is a hydrocarbon radical comprising 6 to 20 main chain carbon atoms, wherein hydrogen atoms bonded to the main chain carbon atoms are optionally substituted; $V_1$ is a saturated or unsaturated, monocyclic or bicyclic ring system comprising 5 to 9 ring atoms, wherein at least 2 ring atoms are nitrogen atoms forming the same cyclic moiety; and $V_2$ is a moiety comprising a carboxyl group and an unsaturated carbon-carbon bond.

12 Claims, 8 Drawing Sheets

| | Composition of Microemulsion (wt%)* | | | | |
|---|---|---|---|---|---|
| Samples | 1 | 2 | 3 | 4 | 5 |
| Water | 26.0 | 20.0 | 26.0 | 25.0 | 25.0 |
| AIPSA | 28.0 | 30.0 | 29.0 | 29.0 | - |
| AUPSA | - | - | - | - | 29.0 |
| AN | - | 15.0 | - | - | - |
| MMA | 25.0 | 23.5 | 30.0 | 20.0 | 30.0 |
| SPM | 20.0 | - | 14.0 | 14.0 | - |
| SPI | - | 10.0 | - | - | 15.0 |
| NAMAP | - | - | - | 8.0 | - |
| A174 | - | - | - | 3.0 | - |
| MBAA | - | 1.5 | - | - | - |
| EGDMA | 1.0 | - | 1.0 | 1.0 | 1.0 |
| Ion Conductivity after treated with 0.5M $H_2SO_4$ | | | | | |
| S/cm | 0.16 | 0.11 | 0.11 | 0.14 | 0.09 |

- Polymerization by UV-initiator: 0.3wt%

| Sample | Composition of precursor microemulsions | | | Appearance | |
|---|---|---|---|---|---|
| | Water | MMA | AIPSA | BP | AP |
| AIPSA-1 | 25 | 37.5 | 37.5 | Clear | Clear |
| AIPSA-2 | 30 | 35 | 35 | Clear | Clear |
| AIPSA-3 | 35 | 32.5 | 32.5 | Clear | Clear |
| AIPSA-4 | 40 | 30 | 30 | Clear | Clear |

FIGURE 7

ION CONDUCTING POLYMERS

This application is a continuation in part of U.S. application Ser. No. 10/176,958 filed on Jun. 21, 2002 now abandoned, which claims the benefit of Singapore patent application no. 200103843-9, both of which are incorporated herein by reference in their entirety.

This invention relates to novel compounds that can be used in the preparation of membranes. In particular, the invention relates to copolymerizable sulfonic acid derivatives which are useful for the preparation of ion conducting membranes. The invention also relates to processes for preparing these compounds and for preparing membranes using these compounds, as well as the membranes incorporating these compounds.

BACKGROUND OF THE INVENTION

Ion conductive polymers find application in several fields of technology, for instance, in electrochemical applications such as proton-exchange fuel cells, batteries, ion exchange membranes and sensors.

It is generally known that emulsions can be formed from a mixture of oil, water and surfactant. A thermodynamically unstable emulsion appears milky while a thermodynamically stable emulsion appears as a transparent colloidal dispersion of oil and water stabilised surfactant, known as a microemulsion.

Microemulsions can have a variety of fluid structures, depending on the components that are comprised in the microemulsion. For example, microemulsions can be in the form of droplets which are swollen with oil and dispersed in water (OW), or they can be swollen with water and dispersed in oil (W/O). Additionally, there may exist bicontinuous microemulsions which have oil and aqueous domains that are randomly interconnected to form sponge-like structures.

The unique fluid structures of microemulsions have been used to provide polymerization loci for monomers. Kuo et al. (Macromolecules, 1987, 20, page 1216) describe the polymerization of styrene in an O/W microemulsion, while Candau et al. (U.S. Pat. No. 4,681,912) describe the polymerization of water soluble monomers in W/O microemulsions.

In order to obtain transparent microporous polymeric materials, various types of reactants have been used in W/O and bicontinuous microemulsion polymer blends. For example, U.S. Pat. No. 5,521,229 discloses the preparation of polymers having a nonporous, bicontinuous structure employing photo-polymerization of microemulsions comprising water, a polar species, a hydrophobic unsaturated monomer, and a polymerizable aliphatic surfactant. Price (U.S. Pat. No. 5,151,217) discloses a bicontinuous microemulsion comprising hydrophobic monomers such as styrene and quaternary ammonium salts as polymerizable surfactant. In addition, European Patent Application No. EP 0 531 005 A2 discloses the use of polar liquids such as alcohols or amides in forming the continuous liquid phase of a bicontinuous microemulsions, in conjunction with quaternary ammonium salts, as polymerizable surfactant.

In general, it is desirable for the ion conductivities of such materials to be as high as possible. Examples of commercial polymer electrolyte membranes, such as those of Nafion (Dupont) which are perfluorosulfonic polymers, and Dais Corporation, which are non-fluorinated membranes made of triblock copolymers with 50% to 60% sulfonation, show conductivity ranging from 0.01 to 0.1 S/cm.

More recently, Peled et al. (*Electrochemical and solid state polymer binder;* 1998; 5:210) synthesized ion conducting membranes which incorporated ceramic powder and polymer binder doped with $CF_3SO_3H/H_2SO_4$. Conductivity of the membrane was reported to be about 0.21 S/cm.

Accordingly, it is an object of the present invention to provide copolymerizable surfactant compounds which are stable, economical to produce, and can be reliably used in a bicontinuous microemulsion polymerization process to be polymerized with a suitable copolymer to give rise to ion conducting membranes having high proton conductivities. It is also an object of the invention to develop routes of synthesis for the copolymerizable surfactant compounds and for the membranes that are derivable from the surfactant compounds which are faster and more economical than existing commercial processes.

SUMMARY OF THE INVENTION

In one aspect, the present invention provides a compound having the general formula (I):

$$^-O_3S—R_1—V_1—R_2—V_2$$

wherein $R_1$ is a hydrocarbon radical comprising 1 to 10 main chain carbon atoms, wherein hydrogen atoms bonded to the main chain carbon atoms are optionally substituted;

$R_2$ is a hydrocarbon radical comprising 6 to 20 main chain carbon atoms, wherein hydrogen atoms bonded to the main chain carbon atoms are optionally substituted;

$V_1$ is a saturated or unsaturated, monocyclic or bicyclic ring system comprising 5 to 9 ring atoms, wherein at least 2 ring atoms are nitrogen atoms, said nitrogen atoms being comprised in the same cycle; and $V_2$ is a moiety comprising a carboxyl group and an unsaturated carbon-carbon bond.

In another aspect, the invention also provides a process for the preparation of a compound of formula (I), $$^-O_3S—R_1—V_1—R_2—V_2$$

wherein $R_1$ is a hydrocarbon radical comprising 1 to 10 main chain carbon atoms, wherein hydrogen atoms bonded to the main chain carbon atoms are optionally substituted;

$R_2$ is a hydrocarbon radical comprising 6 to 20 main chain carbon atoms, wherein hydrogen atoms bonded to the main chain carbon atoms are optionally substituted;

$V_1$ is a saturated or unsaturated, monocyclic or bicyclic ring system comprising 5 to 9 ring atoms, wherein at least 2 ring atoms are nitrogen atoms, said nitrogen atoms being comprised in the same cycle;

$V_2$ is a moiety comprising a carboxyl group and an unsaturated carbon-carbon bond; said process comprising:

a) reacting a compound having a saturated or unsaturated, monocyclic or bicyclic ring system comprising 5 to 9 ring atoms, wherein at least 2 ring atoms are nitrogen atoms that are comprised in the same cycle, with an alcohol having the structure:

$$X'—R_2—OH$$

wherein $X'$ is a halogen, and $R_2$ is a hydrocarbon radical comprising 6 to 20 main chain carbon atoms, wherein hydrogen atoms bonded to the main chain carbon atoms are optionally substituted;

b) reacting the product obtained from a) with a sultone; and c) reacting the product obtained from b) with compound having the structure (IIa):

$$X-\overset{O}{\underset{\|}{C}}-\overset{R_3}{\underset{|}{C}}=C\overset{R_4}{\underset{R_5}{\diagdown}}$$

wherein

X is halogen; and $R_3$, $R_4$ and $R_5$ are independently selected from the group consisting of H and $C_1$–$C_4$ alkyl, optionally substituted.

In yet another aspect, the invention provides a process for producing an ion conducting membrane, comprising copolymerizing at least one copolymerizable surfactant with a copolymerizable monomer in a bicontinuous microemulsion polymerization mixture comprising:

i) about 15% to 50% by weight of water;

ii) about 10% to 50% by weight/weight of at least one copolymerizable surfactant having the of formula (I), $$^-O_3S-R_1-V_1-R_2-V_2$$

wherein $R_1$ is a hydrocarbon radical comprising 1 to 10 main chain carbon atoms, wherein hydrogen atoms bonded to the main chain carbon atoms are optionally substituted;

$R_2$ is a hydrocarbon radical comprising 6 to 20 main chain carbon atoms, wherein hydrogen atoms bonded to the main chain carbon atoms are optionally substituted;

$V_1$ is a saturated or unsaturated, monocyclic or bicyclic ring system comprising 5 to 9 ring atoms, wherein at least 2 ring atoms are nitrogen atoms, said nitrogen atoms being comprised in the same cycle; and $V_2$ is a moiety comprising a carboxyl group and an unsaturated carbon-carbon bond; and iii) about 5% to 40% by weight of at least one copolymerizable monomer;

wherein said weight percents are based on the total weight of the microemulsion.

In yet a further aspect, the invention provides an ion conducting membrane comprising a copolymer, wherein said copolymer comprises a monomer having the general formula (I):

$$^-O_3S-R_1-V_1-R_2-V_2$$

wherein $R_1$ is a hydrocarbon radical comprising 1 to 10 main chain carbon atoms, wherein hydrogen atoms bonded to the main chain carbon atoms are optionally substituted;

$R_2$ is a hydrocarbon radical comprising 6 to 20 main chain carbon atoms, wherein hydrogen atoms bonded to the main chain carbon atoms are optionally substituted;

$V_1$ is a saturated or unsaturated, monocyclic or bicyclic ring system comprising 5 to 9 ring atoms, wherein at least 2 ring atoms are nitrogen atoms, said nitrogen atoms being comprised in the same cycle;

$V_2$ is a moiety comprising a carboxyl group and an unsaturated carbon-carbon bond.

BRIEF DESCRIPTION OF THE DRAWINGS

The invention will be better understood with reference to the detailed description when considered in conjunction with the non-limiting examples and the drawings, in which.

DETAILED DESCRIPTION

The present invention is based on the finding that compounds having a sulfonic acid group and a copolymerizable hydrocarbon chain attached to a heterocyclic ring system possess excellent characteristics as surfactants. Produced by means of a 3-step synthesis route, the present surfactants can incorporate various types of heterocyclic ring systems, resulting in surfactants that can be anionic (owing to the negatively charged sulfonic acid group and an uncharged ring system) or zwitterionic (where ring system acquires a positive charge). The present inventors also discovered that when these surfactants are used in the preparation of ion conducting membranes (ICMs), the resulting ICMs have conductivities that are comparable if not better than those of commercially available ICMs.

$R_1$ in the above formula (I) of the compound of the present invention denotes a hydrocarbon radical comprising 1 to 10, preferably 2 to 7, or more preferably 3 or 4, main chain carbon atoms. $R_2$ denotes a hydrocarbon radical comprising 6 to 20, or preferably 8 to 16, more preferably 11 to 12 main chain carbon atoms. R1 and R2 can be chosen independently. In general, the chain lengths of $R_1$ and/or $R_2$ may be increased or decreased to vary the solubility and/or other properties of the surfactant. Therefore, when used in a microemulsion, varying the chain lengths of $R_1$ and/or $R_2$ in the compounds of the invention allows to provide different microemulsion systems having different phase properties.

In principle, any hydrocarbon structure is suitable as $R_1$ and $R_2$. For example, $R_1$ and $R_2$ as defined in formula (I) above can be a straight chained or branched, substituted or unsubstituted alkyl, alkenyl, alkynyl, cycloalkyl, cycloalkenyl, aryl or arylalkyl group/radical. When the compounds of the present invention are used as polymerizable surfactants in microemulsion polymerization processes, $R_1$ and $R_2$ are preferably saturated, branched or straight-chained alkyl or cycloalkyl groups.

Alkyl groups as used herein may be straight chained or branched. This also applies if they are present in other groups such as alkoxy groups, alkoxycarbonyl groups or in amino groups, or if they are substituted. Alkyl groups that are used in compounds having formula (I) may have 1 to 30 carbon atoms in total, and include groups such as methyl, ethyl, propyl, isopropyl, n-propyl, butyl, n-butyl, tert-butyl, pentyl, n-pentyl, iso-pentyl, n-hexyl, iso-hexyl, heptyl, octyl, nonyl, decyl, undecyl, dodecyl and pentadecyl groups.

Examples of alkenyl groups include all aliphatic hydrocarbons having at least one carbon-carbon double bond. In this context, alkenyl radicals when used as main chain radicals can have 2 to 20 carbon atoms.

Examples of alkynyl radicals are straight-chained or branched hydrocarbon atoms which contain at least one triple carbon-carbon double bond. In this context, alkinyl radicals when used as main chain radicals may have 2 to 20 carbon atoms.

Cycloalkyl radicals are saturated cyclic hydrocarbons which normally contain three to eight ring carbon atoms, preferably five or six ring carbon atoms. Cycloalkyl radicals may in turn be substituted. Examples of cycloalkyl radicals are cyclopropyl, cyclobutyl, cyclopentyl, cyclohexyl, cycloheptyl and cyclooctyl, all of which may also be substituted, for example, by one or more identical or different $(C_1-C_4)$— alkyl radicals, in particular by methyl. Examples of such substituted cycloalkyl radicals are 4-methylcyclo-hexyl or 2,3-dimethylcyclopentyl.

Cycloalkenyl radicals are unsaturated cyclic hydrocarbons which normally contain three to eight ring carbon atoms. Cyoloalkenyl radicals have at least one carbon-carbon double bond, but may have 2 or more double bonds. Cycloalkenyl radicals may in turn be substituted.

Cycloalkylalkyl radicals are saturated hydrocarbons which are derived from a cycloalkyl-substituted alkyl group. The cyoloalkyl group normally has five to six ring carbon atoms. Examples of cycloalkylalkyl radicals are cyclopentylmethyl, cyclopentylethyl, cyclohexyl-ethyl and, in particular, cyclohexylmethyl. Cycloalkylalkyl radicals may in turn be substituted.

Examples of aryl radicals are carbocyclic or heterocyclic aromatic radicals, preferably phenyl, naphthyl or heteroaryl. Aryl radicals may also be unsubstituted or substituted with substituents such as halogens, alkyls, phenyls, hydroxyls, and carboxyls.

Halogen as used herein refers to chlorine, bromine, fluorine and iodine.

Arylalkyl radicals which may be used in particular are benzyl, phenethyl and naphthylmethyl groups. All groups may be optionally substituted or polysubstituted, for example, with a halogen, hydroxy, amino, nitro, nitrile, alkoxy, or a carboxyl group.

In formula (I), $V_1$ is a saturated or unsaturated, monocyclic or bicyclic ring system, comprising a total of 5 to 9 ring atoms. Typically, ring atoms are selected from the group consisting of C, N, O, or S. In the present invention, at least 2 ring atoms of the ring system are nitrogen atoms that are comprised in the same cycle. This means that the ring system is typically a heterocyclic compound. The at-least-2 nitrogen atoms of the ring system as defined in formula (I) are each substituted with a hydrocarbon chain. One hydrocarbon chain carries a copolymerizable group which may be copolymerized with another monomer, while the other chain that is attached to the ring system carries a sulfonate group which, when ionized and hydrated in the presence of water molecules, can confer or improve solubility in aqueous solution. This structure was found to be advantageous for producing ICMs having better conductivities.

In an embodiment, polymerizable surfactant compounds of formula (I) possess a ring system $V_1$ which is an unsaturated or aromatic, 5 or 6 membered monocyclic ring system. Examples of such ring systems include imidazole. Essentially, these monocyclic ring systems provide nitrogen atoms which can be substituted with the required hydrocarbon chains. For example, a secondary amine group can react with a halogenated alcohol having a hydrocarbon structure of R1 in order to attach R1 to the ring system. In a further embodiment, the 5 or 6 membered monocyclic ring system is selected from the group consisting of imidazole, pyrazole, 1,2,4-triazole, tetrazole, and pyrazine.

In another preferred embodiment, the ring system of $V_1$ is a saturated, 5 or 6 membered monocyclic ring system. Examples of such saturated 5 or 6 membered ring systems include piperazine, imidazoline, thiolane, and 1-oxa-3-thia-5-azolane.

In a further embodiment, the bicyclic ring system of $V_1$ is an unsaturated, 9 membered bicyclic ring system. Such a bicyclic ring system may comprise 2 heterocyclic rings that are fused together, or a heterocyclic ring that is fused with a non-heterocyclic ring. Examples of such bicyclic ring systems are benzimidazole, purine, indazole, 1H-pyrazolo[4,3-d]oxazole, 4H-imidazo[4,5-d]thiazole, pyrazino[2,3-d]pyridazine, imidazo[2,1-b]thiazole, imidazo[1,2-b][1,2,4]triazine, and 4H-1,3-dioxolo-[4,5-d]imidazole. Particularly suitable bicyclic ring systems are benzimidazole, purine and indazole.

When compounds of the present invention are used as polymerizable surfactants in the preparation of ion conducting membranes, the ring system $V_1$ can be selected according to the desired membrane properties. For example, if it is desired to obtain membranes that are proton conducting, the compound may incorporate a ring system such as imidazole. If it is intended to facilitate proton transfer in membranes, a ring system such as piperazine may be incorporated. If membranes with improved mechanical properties are to be obtained, a ring system such as benzimidazole may be used in the compounds of the invention.

In the compound having formula (I), $V_2$ is a moiety comprising a carboxyl group and an unsaturated carbon-carbon bond. Typically, moieties having these groups include acrylate radicals, methacrylate radicals, or substituted derivatives thereof, such as methyl acrylate, ethyl acrylate, methyl methacrylate or ethyl methacrylate.

In a preferred embodiment, $V_2$ has the formula (II):

wherein $R_3$, $R_4$ and $R_5$ are independently selected from the group consisting of H and a $C_1$–$C_4$ alkyl group, optionally substituted.

In general, as stated above, the compounds of the present invention can usually be used as surfactants and can thus be used in various practical applications, for instance, as additives in the production of water-based polymer emulsions, as a monomer in the preparation of copolymer emulsions, from which substances such as paints, inks, adhesives and textile coatings are obtained, or for biomedical research, e.g., bacterial stains. Several classes of compounds having formula (I) were also found to be capable of providing ion conducting membranes with good conductivities. One class of compounds of the invention according to formula (I) which have been found to be particularly suitable as a polymerizable surfactant has the following formula (III):

wherein $1 \leq m \leq 10$ and $6 \leq n \leq 20$.

Another class of compounds that has been found to be particularly suitable as a polymerizable surfactant is a compound having the formula (IV):

where $6 \leq n \leq 20$, $1 \leq m \leq 10$, $X=Na^+$, $Li^+$, or $NH_4^+$, and V is (methyl)acrylate or another copolymerizable unsaturated group. In aqueous solution, this compound may acquire a negative charge. In the above salt, X can also be H, K, or any other metal that can have an oxidation state of 1.

The skilled person will understand that all possible enantiomers and diastereomers of the compounds having the general formula (I), as well as mixtures of two or more stereoisomeric forms in all possible ratios, are contemplated to be within the scope of the invention.

Figure 6A:
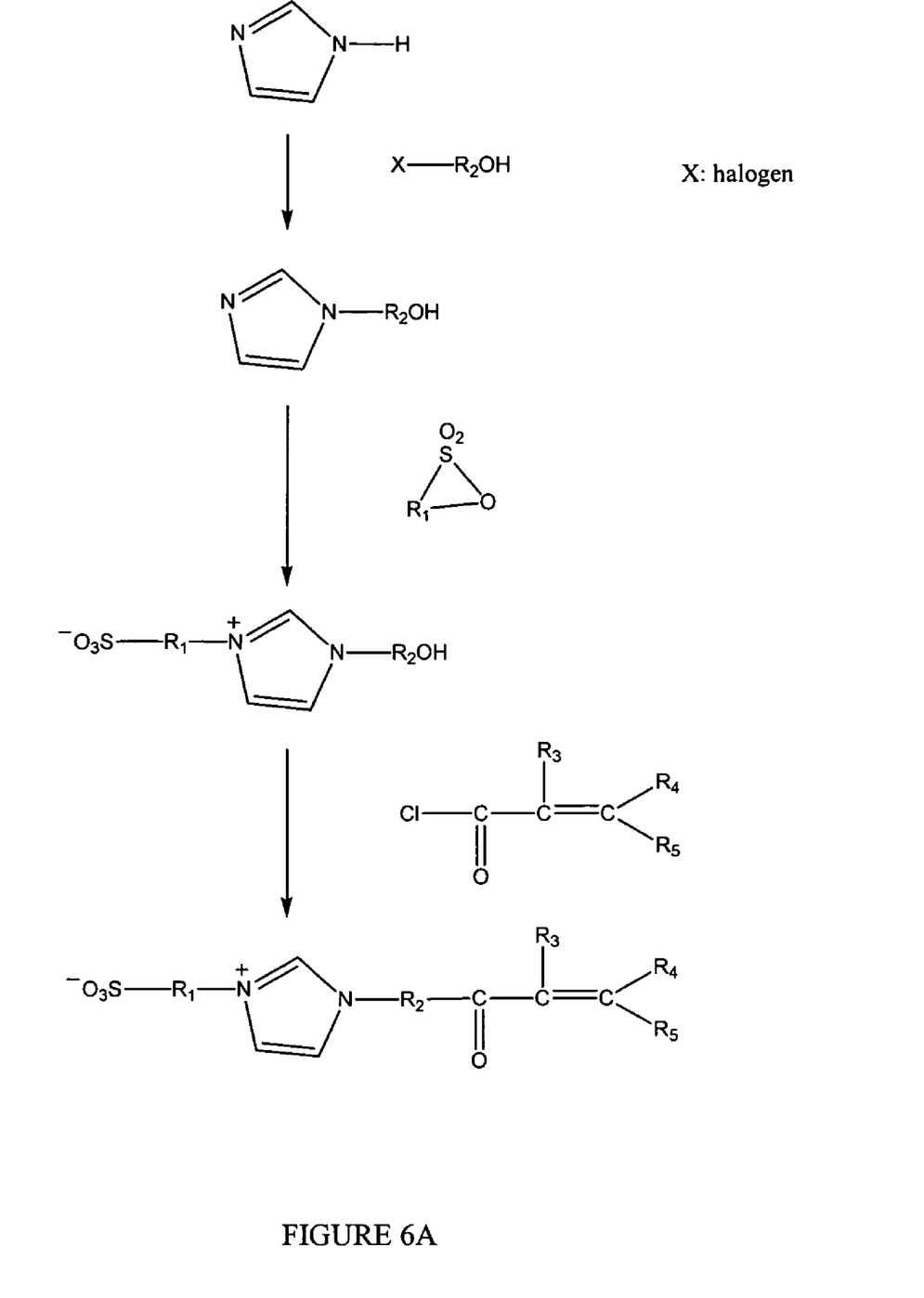
FIG. 6A shows a general synthesis route for obtaining copolymerizable surfactants of the present invention having an unsaturated ring system.
Figure 6B:
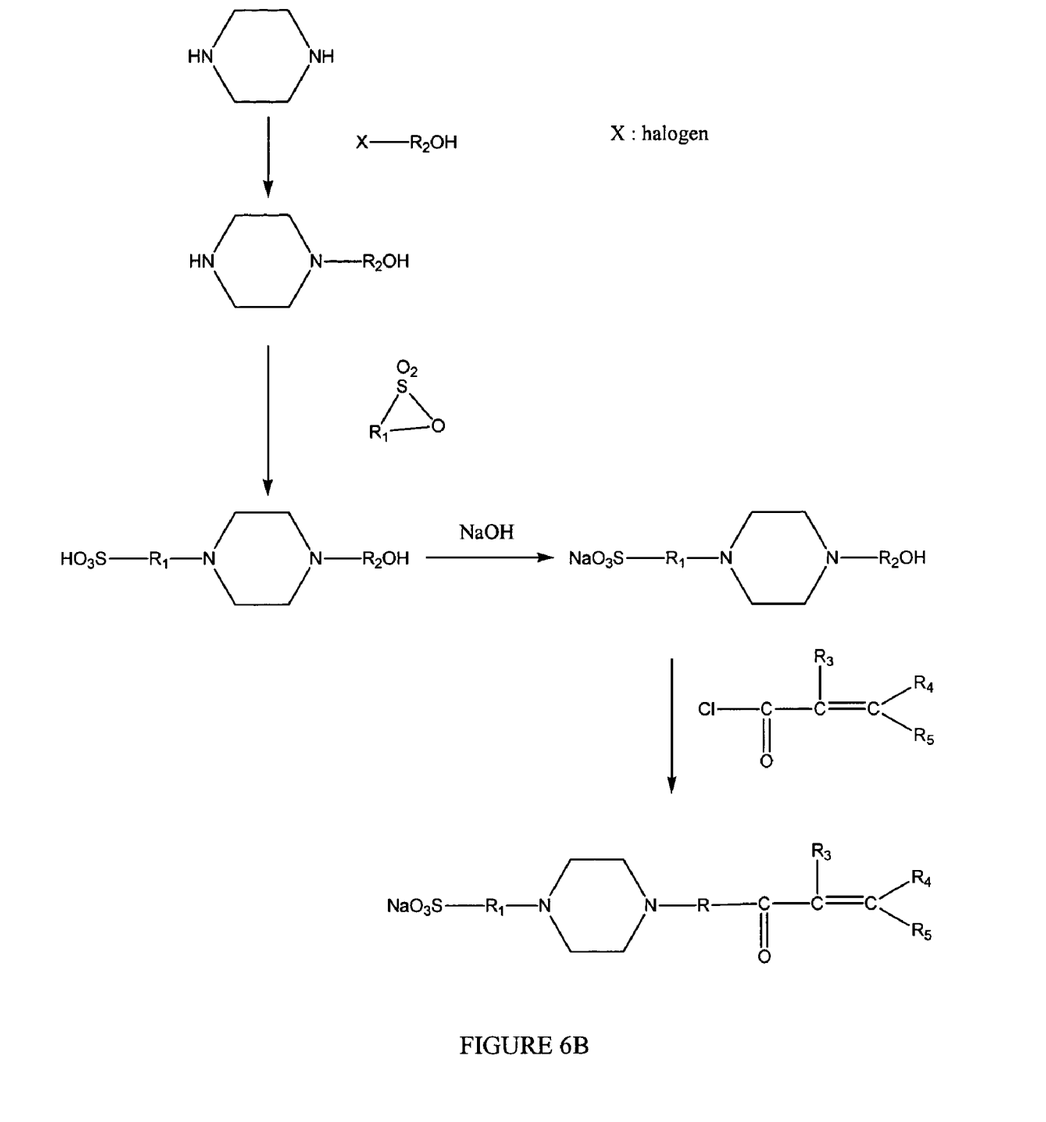
FIG. 6B shows a general synthesis route for obtaining copolymerizable surfactants of the invention having an saturated ring system.

The invention is also directed to a method of preparing compounds having formula (I). This synthesis route, which is illustrated in FIGS. 6A and 6B, is a 3-step process and is described in detail as follows.

First, a molecule having the saturated or unsaturated monocyclic or bicyclic ring system as defined for V, above is reacted with a halogenated alcohol comprising 6 to 20 main chain carbon atoms, i.e. which main chain corresponds to $R_2$ above. The halogenated alcohol attacks one of the at-least-2 nitrogen atoms in the ring system to form a hydroxy intermediate. Several mechanistic routes may be applicable to the reaction; a commonly known mechanism is the substitution nucleophilic bimolecular ($SN_2$) mechanism. Regardless of the mechanistic route assumed, the reaction can be carried out as shown in the Examples below.

Any suitable alcohol having 6 to 20 main chain carbon atoms and having at least 1 halogen-substituted main chain carbon atom, in particular a terminal main chain carbon atom, may be used as a halogenated alcohol. Examples are iodohexan-1-ol, bromoundecan-1-ol, bromopentadecan-1-ol, chloroicosan-1-ol, 3-bromo-cyclohexen-1-ol.

This first reaction step may be carried out in any suitable reaction medium, for example in an alkaline alcoholic medium. Suitable alkaline mediums can be prepared by mixing aqueous NaOH, KOH or Ca(OH)$_2$ solution containing an alcohol which is water miscible. Examples of suitable alcohols are methanol, ethanol, propanol, isopropanol or 1-butanol. The components of the reaction can be added in any sequence. For example, after the reaction medium is prepared, the halogenated alcohol and ring system compound of $V_1$ may be added to it. It is also possible to add the reaction medium reagents to a mixture of halogenated alcohol and ring system compound. It is also possible to add the reaction medium reagents to one of the reactants before adding the second reactant. The reaction is usually carried out under reflux at elevated temperatures. Typically, temperatures of 60 to 80 degrees Celsius are used.

The hydroxy intermediate thus obtained can be directly used to carry out the second step without any further processing, or if necessary, it is washed and dried prior to further reaction. Steps which may be carried out to purify the precipitate includes, for example, evaporating the alcohol medium, dissolving the white precipitate in an organic solvent such as ether and re-precipitating the precipitate in water, and also drying the precipitate until constant weight is achieved prior to carrying out the second step.

In the second step of the process, sulfo-alkylation may be carried out. In this case, the hydroxyl intermediate that is obtained as explained above is reacted with a sultone to covalently link an alkyl sulfonate group to the second nitrogen atom in the ring system of $V_1$ to produce a sulfonate intermediate. The process of sulfo-alkylation is known and described, for example, in U.S. Pat. No. 2,366,007, which is incorporated herein by reference.

Any suitable sultone can be used in the process of the invention, as long as it provides the required hydrocarbon structure that corresponds to the that of $R_1$.

Examples of sultones that can be used in this process include 1,3-propanesultone, 1,4-butanesultone, 1,5-pentanesultone, 1,6-hexanesultone, 1,7-heptanesultone, 1,8-octanesultone, 1,8-naphthosultone, 1-butane sulfonic acid 3-hydroxysultone, 2-butane sulfonic acid 4-hydroxysultone, 2-pentane sulfonic acid 4-hydroxysultone, 2-methyl-2-pentane sulfonic acid 4-hydroxysultone, 4-heptane sulfonic acid 6-hydroxysultone; 1-heptane sulfonic acid 3-hydroxysultone, 1-heptane sulfonic acid 4-hydroxysultone; 6-methyl-1-heptane sulfonic acid 3-hydroxysultone, 3 methyl-4-heptane sulfonic acid 2-hydroxysultone, which are commercially available or can be synthesized via known synthesis routes.

An example of a suitable synthesis route for obtaining the above sultones is disclosed in U.S. Pat. No. 3,115,501. In general, the synthesis route disclosed in this reference can provide substituted sultones having the following general structure:

where R is a hydrogen atom or an alkyl radical and R' is methylene or R-substituted methylene.

Another example of an applicable sultone synthesis route is disclosed in *Organic Syntheses*, CV4, 529. The synthesis route disclosed therein generally uses sodium sulfite and bis-chloroalkyl ether to produce a sodium sulfite ether. This sodium sulfite ether is then cyclized by using an ion-exchange resin at elevated temperatures to yield the sultone. Starting from bis-chloroalkyl ethers such as bis-3-chloropropyl ether, bis-4-chlorobutyl ether, bis-5-chloropentyl ether, bis-6-chlorohexyl ether, bis-7-chlorohexyl ether, and bis-8-chlorooctyl ether, the respective sultones providing the desired hydrocarbon structure of the $R_1$ main chain can be easily obtained. Also, the process described in U.S. Pat. No. 3,100,779 may be used to obtain sultones which can be used in the present process.

Alternatively, the sulfonate intermediate can be obtained by nucleophilic substitution of a corresponding halogenated sulfonate derivative whereby the nucleophilic unsubstituted nitrogen atom in the ring system attacks the carbon atom carrying the halogen atom in the sulfonic acid derivative. A suitable halogenated sulfonate derivative may have the general structure:

wherein X and $R_1$ are as defined above. Examples of suitable sulfonic acid derivatives are sodium salts of n-1-butane sulfonic acid, n-1-pentane sulfonic acid, n-1-hexane sulfonic acid and n-1-decane sulfonic acid all of which are available from NorQuay Technologies Inc.

Another alternative for obtaining the sulfonated compound that carries the R1 chain (cf. FIG. 6) from the hydroxy intermediate, is to provide a sulfonic acid compound HO—$(R_1)$—$SO_3^-$ (VII) which is then reacted with the hydroxylated intermediate. For this purpose, one possible reaction to follow is the reaction as described in Tasaur, S. L. & Fitch R. B. JJ Colloid Interface Sci, 1987, 115, 450. This can be done, for example, by reacting an unsaturated alcohol such as undec-10-en-1-ol or dec-10-en-1-ol with sodium sulfite and sodium bisulfate in a molar ratio of 2:1:1, in the presence of ferric chloride, a peroxydisulfate compounds such as sodium peroxydisulfate and benzoyl peroxide to form the hydroxylated sulfonate compound such as hydroxyundecane-1-sulfonate or hydroxydecane-1-sulfonate. The compound (VII) is then reacted with the hydroxylated intermediate described above. The compound (VII) can also be converted into a halogenated sulfonate X—$(R_1)$—$SO_3^-$ which can then used for the further synthesis.

In the third step of the process, the sulfonate intermediate is reacted with a compound having the formula (IIa):

wherein

X is a halogen selected from F, Cl, Br, and I; and $R_3$, $R_4$ and $R_5$ are independently selected from the group consisting of H and $C_1$–$C_4$ alkyl group, optionally substituted.

This step introduces a polymerizable group, such as an acrylate or methacrylate group, into the sulfonate intermediate, thereby forming a polymerizable surfactant that can be copolymerized with another copolymerizable monomer. Where $R_1$ and $R_2$ possess unsaturated groups, it is also possible to copolymerize such unsaturated groups in $R_1$ and $R_2$ with a copolymerizable monomer. In some compounds that are particularly suited for use as polymerizable surfactants, only a terminal C—C double bond is present.

It is known in the art that the synthesis of polymerizable surfactants may be hampered by the presence of spurious polymerization of the polymerizable group. Thus in carrying out the third step, the second polymerization inhibitors can be used to prevent spurious polymerization reactions from taking place.

Another aspect of the invention concerns a process for producing an ion conducting membrane by copolymerizing at least one copolymerizable surfactant with a copolymerizable monomer in a bicontinuous microemulsion polymerization mixture. Copolymerization of organic components in a bicontinuous microemulsion precursor facilitates the synthesis of polymers with an extensive system of randomly distributed interconnected aqueous channels. When the polymer is dried to remove the aqueous liquid in the channels, an extensive system of pores with sizes ranging between 10 to 30 nm forms when the copolymer is formed. The unique pore nanostructure of the aqueous phase results from the fast copolymerization of all polymerizable organic components in the precursor mixture. Additionally, rapid copolymerization initiated by redox or photo initiators at low temperatures helps to ensure that nanostructural stability is maintained during polymerization. Furthermore, the process by which copolymerization is carried out is simple, being only a one-step process, and thus economical. Membranes of the present invention are suited for use in electrochemical applications such as fuel cell membranes and biosensors.

A thermodynamically stable microemulsion of oil and water can be stabilized with a surfactant, and if necessary, with a co-surfactant. However, depending on the surfactant that is used, a co-surfactant may not be necessary. Surfactants such as non-ionic surfactants, double-chain surfactants or cationic surfactants do not require the assistance of co-surfactants. An example of a known double-chain surfactant is sodium 1,4-bis(2-ethylhexyl) sulfosuccinate, which is commonly known as Aerosol OT.

Figure 1:
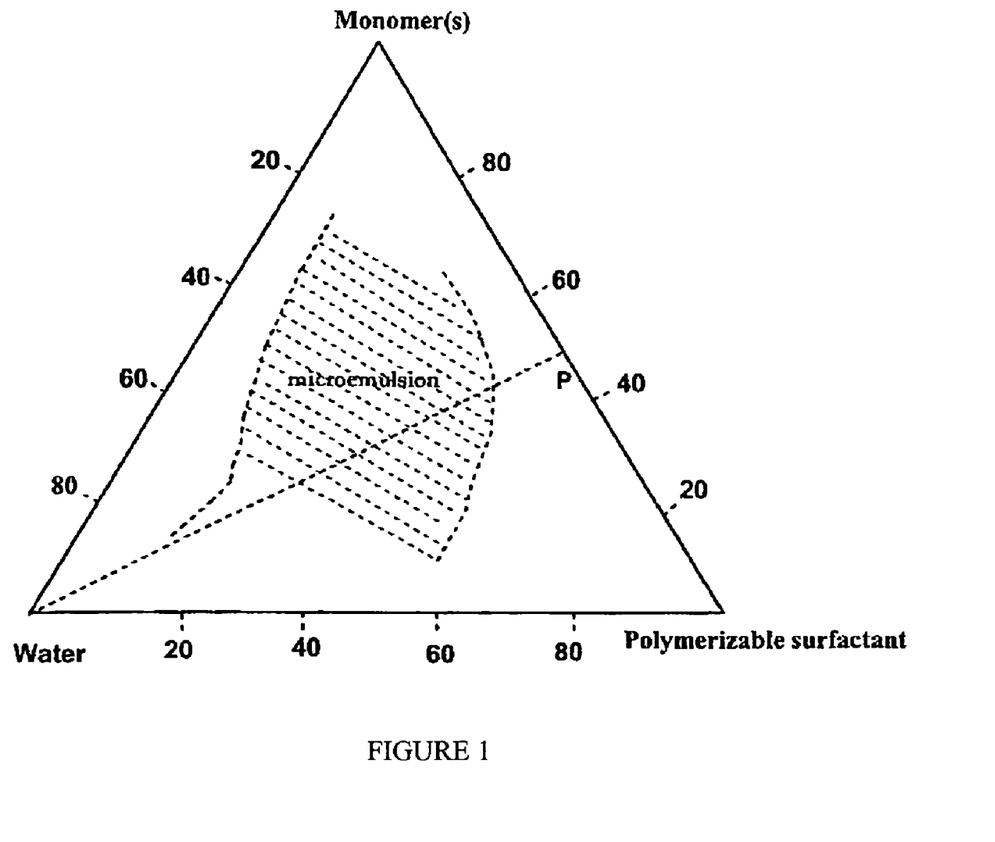
FIG. 1 shows a typical ternary phase diagram of a monomer/surfactant/water mixture at 25° C., where 3-[(11-acryloyloxyundecyl)-imidazolyl] propyl sulfonate (AIPSA) is used as an example of a compound of the present invention; the single-phase microemulsion region of the diagram is represented by a dotted area, and mixtures having compositions falling within the dotted area are used in the present invention.
Figure 2:
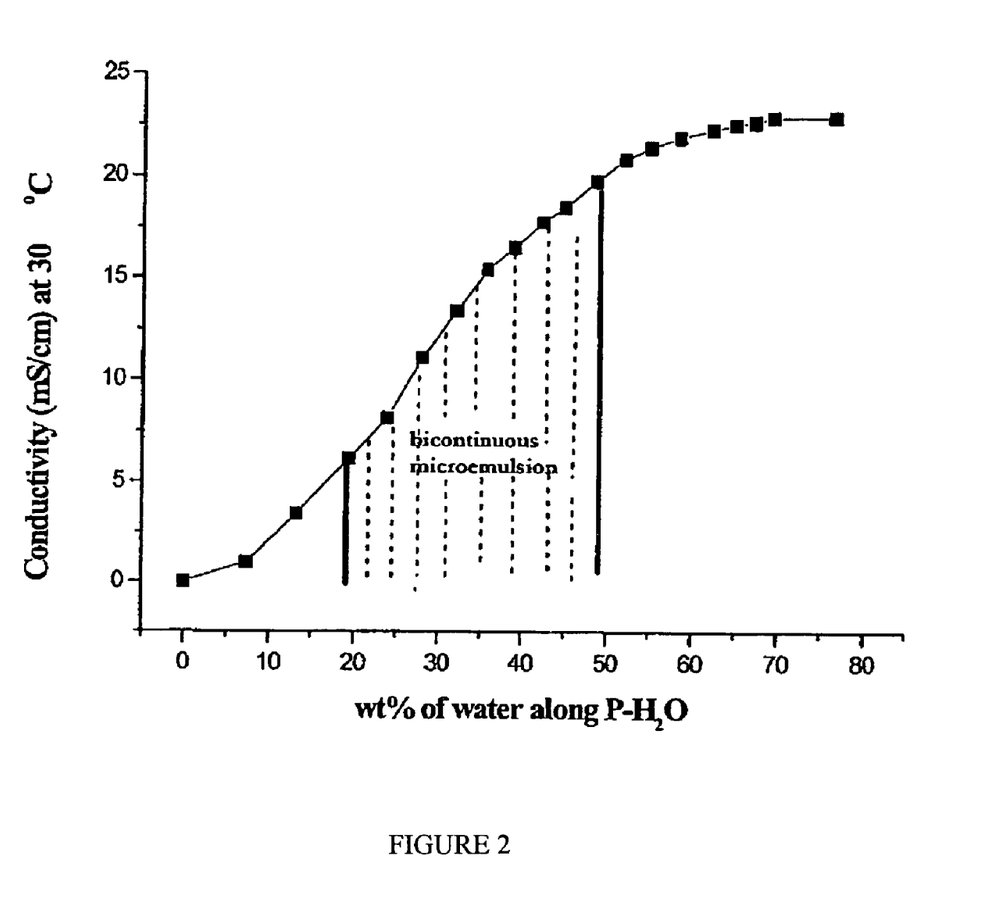
FIG. 2 shows a typical conductivity plot indicating an approximate composition region for bicontinuous microemulsions; the ionic conductivity of the mixture can be seen to increase substantially in the bicontinuous microemulsion region using AIPSA.

In the method of the invention for preparing membranes, the composition of the bicontinuous emulsion used for polymerization is one which is chosen to fall within the microemulsion region (cf. FIG. 1) in the water-surfactant-monomer composition chart. When a microemulsion has a composition falling within this region, the microemulsion is considered to be thermodynamically stable. Further within that region, the composition of the bi-continuous microemulsion is optimally chosen to correspond to the water composition at which ionic conductivity increases substantially in the conductivity vs. water composition graph characterizing the ionic conductivity of the water composition graph (cf. FIG. 2).

Although the production of bicontinuous structural materials by microemulsion polymerization is known in the art (U.S. Pat. Nos. 5,151,217, 5,521,229 and EP Patent Application No. 0 531 005), the ability to produce polymeric membranes of high ionic conductivity (0.1–0.2 S/cm) by a single step process of microemulsion copolymerization is only disclosed in the present invention. This is advantageously accomplished by the low temperature (<35 degrees Celsius) microemulsion polymerization of ionic or non-ionic monomers and polymerizable surfactants in the presence of redox or photo initiators.

In general, when appropriate amounts of the components are mixed, a thermodynamically stable microemulsion forms spontaneously. The present inventors have discovered that such a phenomenon can be used favorably to carry out polymerization of monomers within the bicontinuous microemulsion. Thus, the present invention is also directed to a process of forming an ion conducting membrane comprising copolymerizing at least one copolymerizable surfactant with a copolymerizable monomer in a bicontinuous microemulsion polymerization mixture which comprises about 15% to 40% by weight of water; about 5% to 50% by weight of at least one copolymerizable surfactant having the formula (I) described above; and about 5% to 40% by weight of at least one copolymerizable monomer can be used to carry out the co-polymerization of monomers to produce an ion conducting membrane. The above weight percentages are based on the total weight of the microemulsion.

In addition to the surfactant having the formula (I), it is possible to include into the microemulsion polymerization mixture other polymerizable surfactants of the following 2 types:

a) Anionic surfactants which are exemplified by the following formula (V):

or b) Non-ionic surfactants which are exemplified by the following formula (VI):

wherein

M is either ammonium or a metal cation;

V is either p-vinylbenzyl, (methyl) acrylate or other copolymerizable unsaturated group;

$R_6$ is either a hydrogen or an alkyl group selected from the group consisting of between $C_1$–$C_5$;

n is an integer from 6 to 20; m is an integer from 4 to 20; and

X is an integer of about 10 to 110.

Other suitable reactive surfactants include but are not limited to those available from PPG Industries Inc., such as the SAM(N) 185–187 series of polymerizable non-ionic surfactants and the SAM(A) 181, 183, 184, 211 series of anionic sulfonates or sulfates.

It will be understood by a person skilled in the art that suitable surfactants are not limited to those given above, as many other types of surfactants may be included in the precursor mixture for use in the method of the present invention. However, the incorporation of the copolymerizable surfactants of the present invention into the copolymer results in copolymers having satisfactory conductivity.

A large number of suitable polymerizable monomers exist which can be used in the above method. In general, a suitable monomer is one which possess a carboxyl group and at least one unsaturated carbon-carbon double bond. Suitable monomers include methyl methacrylate, acrylonitrile, and butyl acrylate. Copolymerizable monocarboxylic acids that can be used in the present method include acrylic acid and methacrylic acid and their derivatives. These derivatives include the C1 to C12 alkyl alcohol esters such as 2,2,3,3,-tetrafluoropropylmethacrylic acid ester; the sodium salt of the esters, namely 3-sulfopropyl (methyl) acrylic acid and glycidyl methacrylate; substituted derivatives such as 2-hydroxylethyl methacrylate, and 2-hydroxylethyl acrylate; vinyl aryl monomers such as styrene a lithium styrene sulfonate or acryloyl-N'-methylpiperazine; and nitriles, namely acrylonitrile and methacrylonitrile. Ionic monomers can also be used, such as 3-sulfopropylmethacrylic acid esters or bis-3-sulfopropyl-itaconic acid ester or [(2-methacryloyloxy)ethyl]dimethyl(3-sulfo-propyl) ammonium hydroxide.

Crosslinking agents can be included in the copolymerization blend in order to increase the degree of crosslinkage in the copolymer. However, it is not critical to include them. Examples of suitable cross-linking agents include glycol dimethacrylate as well as diethylene glycol dimethacrylate, diethylene glycol diacrylate and γ-methacryloxy-propyl-trimethoxy silane.

Initiators that can be used to initiate the copolymerization reaction in the present method include photo-initiators such as 2,2-dimethoxy-2-phenyl acetophenone and di-benzylketone. Redox initiators that can be used include ammonium persulfate and N,N,N',N'-tetramethylethylene diamine.

Various additives can optionally be added to the aqueous component. These additives include fillers, dyes, inorganic electrolytes and pH adjusters.

In general, in order to carry out the copolymerization reaction, a precursor mixture is first formed by mixing the required components and then applying the mixture on a reaction surface. Subsequently, initiator is added to the mixture to initiate polymerization. After a desired period of time, the polymer becomes set and hardens to form a polymer film. The polymer film can be used directly or can be subjected to further processing to form an ion conducting membrane. It is not necessary to adhere to the above sequence of forming the polymer, however. The skilled person will appreciate that in order to cast the polymer into different forms according to the requirements of the end product, the above procedure can be suitably adapted.

Polymeric materials of the present invention can be easily fabricated into films/membranes, sheets and surface coating on other membranes/materials by coating/impregnating the mixture on other materials such as papers, glass fibre sheets or other polymer membranes, before an initiator is added. Since a major application of surfactant and polymers of the present invention is in the formation of membranes, it is often desirable to form the resultant polymer into a thin sheet. This can be achieved, for instance, by sandwiching the mixture between two chemically inert plates, e.g. glass, and then carrying out polymerization.

Bicontinuous microemulsions form spontaneously upon mixing a suitable proportion of components, so it may not be necessary to provide mechanical agitation of the polymerization blend. However, the mixture may be stirred as much as necessary to homogenize or mix the microemulsion. Reaction occurs readily in the presence of an initiator around room temperature via free radical polymerization. The rapidity of reaction can be observed within 10 to 20 minutes, by which time the fluid microemulsion is converted into transparent gels. In order to obtain mechanically strong polymeric materials, for example in industrial applications where larger dimensions are required, several hours of polymerization may be needed.

The aqueous phase in the domains can readily be removed by drying, leaving behind a system of vacant pores. Other polar solvents, such as ethylene carbonate or electrolyte solutions can be introduced into the vacant domains. It will be appreciated by the skilled person that such polar solvents may confer beneficial properties on the resultant polymer, and the selection of the solvent to be introduced into the vacant domains will depend upon the intended application of the polymer.

Figure 3:
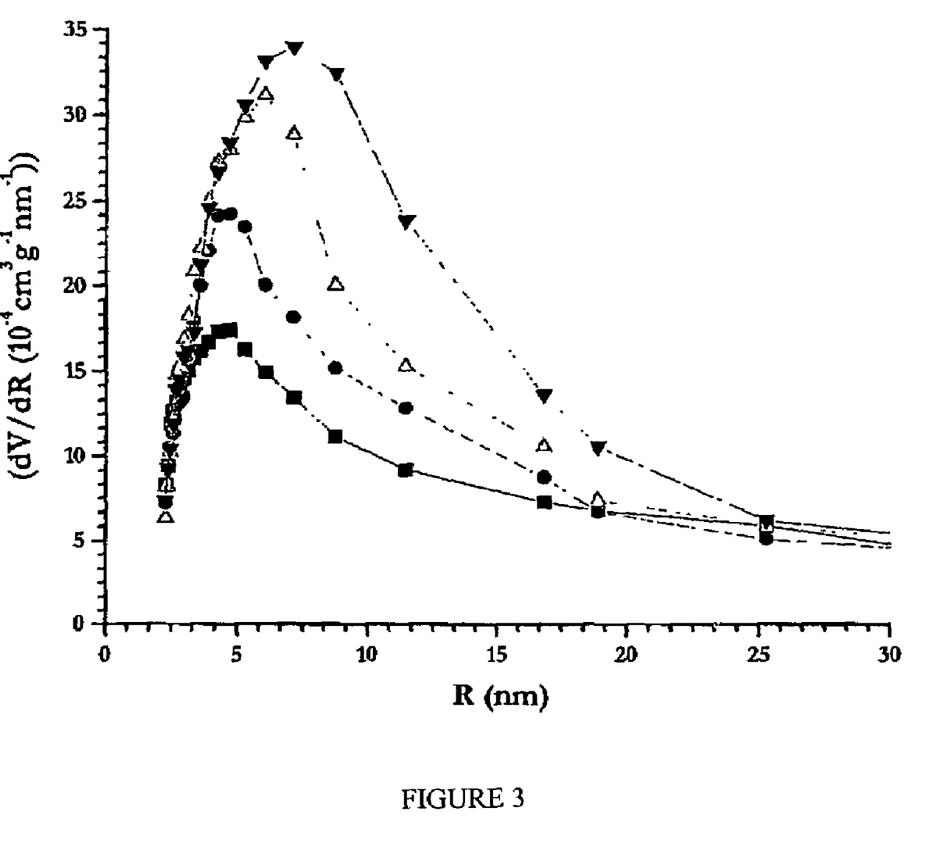
FIG. 3 shows a typical pore size distribution for a membrane incorporating the surfactant AIPSA.

Typical pore size distributions for membranes fabricated using polymers produced by methods embodying the present invention are shown in FIG. 3. It can be seen that the vast majority of aqueous domains in the membranes have diameters in the region of 10 nm to 30 nm. However, the aqueous domains may have diameters of up to 100 nm.

The number of aqueous domains per unit volume of a polymer embodying the present invention will vary depending upon the size of the aqueous domains. In an embodiment of the present invention, the density of aqueous domains is at least $3*10^3/\mu m^3$, and may be as high as $3.5*10^5/\mu m^3$.

In addition to the desirable performance of membranes of the invention and the methods thereof, the fact that the method of the present invention effectively involves only a single step (i.e. the co-polymerization of substantially all of the organic components in the precursor mixture) makes it possible to produce polymers economically.

EXAMPLES

Surfactants Having Unsaturated Ring Systems

One general synthesis route for surfactant compounds of the present invention having a monocyclic or bicyclic unsaturated or aromatic ring system is shown in FIG. 6a. This synthesis route has been applied in the following examples to demonstrate how specific examples of these surfactant compounds are made.

Example 1

Synthesis of Zwitterionic Copolymerizable Surfactant 3-[(11-acryloyoxyundecyl)-imidazolyl] propyl sulfonat (AIPSA)

1.1. Synthesis of 11-hydroxyundecylimidazole (HUI)

First, the synthesis of 11-hydroxyundecylimidazole (HUI) is carried out as follows. 11-bromoundecan-1-ol (25.0 g, 0.1 mol), imidazole (0.08 mol), and 4 g of sodium hydroxide pellets (dissolved in 6 ml of water) in 200 ml of ethanol were refluxed for 6 hours. Upon cooling to room temperature, the precipitate was filtered and the solvent was evaporated. After evaporating off the ethanol, the residue was dissolved in ether, washed twice with water and left to dry overnight by magnesium sulfate. A white solid product was obtained after evaporation of the solvent and dried to a constant weight in vacuum.

Experimental data for the syntheses are summarized along with the elemental microanalytical data for the products. The $^1$H N.M.R. assignments are as follows:

$^1$H N.M.R. (300 MHz, CDCl$_3$): d (in ppm)=1.11–1.7m (18H, —CH$_2$—(CH$_2$)$_7$—CH$_2$—), 3.6t (2H, —CH$_2$—O), 4.0t (2H, N—CH$_2$—), 6.9–7.1d l7.8s (1H, each C$_3$N$_2$H$_3$).

IR (KBr pellet): selected bands: 3348 cm$^1$ (O—H stretch), 2920, 2850 cm$^1$ (C—H stretch), 1500,1600 (C=C ring stretch), 1435,1460 (O—H bend)

Elemental Analysis: C$_{14}$1l$_{26}$N$_2$O

| Calculated | C 70.58% | H 10.92% | N 11.76% | O 6.74% |
| Experimental | C 70.60% | H 10.81% | N 11.70% | O 6.89% |

1.2. Synthesis of 3-((11-hydroxyundecyl)-imidazolyl) propyl sulfonate (HUIPS)

Then the synthesis of 3-((11-hydroxyundecyl)-imidazolyl) propyl sulfonate (HUIPS) was carried out. To a magnetically stirred solution of 11-hydroxyundecylimidazole (0.1 mol) in 200 ml dried acetonitrile, 1,3 propane-sultone (0.1 mol) was added dropwise over 30 minutes. The solution was refluxed for one day under nitrogen atmosphere. The product precipitated out from the reaction mixture and was filtered off. The product was then dried in a vacuum oven for one day at ambient temperature.

Experimental data for the syntheses are summarized along with the elemental microanalytical data for the products. The $^1$H N.M.R. assignments are as follows:

$^1$H N.M.R. (300 MHz, D$_2$O): ~(in ppm)=1.11–1.7m (18H, —CH$_2$—(CH$_2$)$_7$—CH$_2$—), 2.4m (2H, S—C—CH$_2$—C—N), 2.9t (2H, —ciH$_2$—S), 3.6t (2H, —CH$_2$—O), 4.4t (2H, —N—CH$_2$), 4.2t (2H, —NtCH$_2$_), 7.5–7.6d/8.8s (1H, each C$_3$N$_2$H$_3$).

IR (KBr pellet): selected bands: 3348 cm$^1$ (O—H stretch), 2920, 2850 cm$^1$ (C—H stretch),1500,1600 cm$^1$ (CrC ring stretch), 1435, 1460 cm$^1$ (O—H bend), 1162 cm$^1$ (S=O stretch).

Elemental Analysis: C$_{17}$H$_{32}$N$_2$O$_4$S

| Calculated | C 56.66% | H 8.88% | N 7.77% | O 17.77% | S 8.92% |
| Experimental | C 56.70% | H 8.81% | N 7.70% | O 17.80% | S 8.99% |

1.3. Synthesis of 3-((11-acryloyloxyundecyl)-imidazolyl) propyl sulfonate (AIPSA)

3-((11-acryloyloxyundecyl)-imidazolyl) propyl sulfonate (AIPSA) was synthesized as follows. Acryloyl chloride (0.3 mol) was slowly added to a magnetically stirred solution of 3-((11-hydroxyundecyl)-imidazolyl) propyl sulfonate (0.1 mol) in dried acetonitrile (200 ml) at 0° C. purged with N$_2$ gas. The mixture was further reacted at room temperature for 3 days. The mixture was filtered and the excess acryloyl chloride and acetonitrile were removed in a rotary evaporator. The residue was dissolved in distilled chloroform, washed twice with saturated sodium bicarbonate solution followed by saturated brine and left to dry overnight by magnesium sulfate. The pure product of 3-((11-acryloylox-yundecyl)-imidazolyl) propyl sulfonate was obtained by re-precipitating the crude product in anhydrous ether. The precipitate was filtered and dried in a vacuum oven.

Experimental data for the syntheses are summarized along with the elemental microanalytical data for the products. The $^1$H and $^{13}$C N.M.R. assignments are as follows:

$^1$H N.M.R. (300 MHz, D$_2$O): d (in ppm)=1.11–1.7m (18H, —CH$_2$—(CH$_2$)$_7$—CH$_2$—), 2.4m (2H, S—C—CH$_2$—C—N), 2.8t (2H, —CH$_2$S), 4.1t (2H, —CH$_2$—O), 4.4t (2H, —N—CH$_2$—), 4.2t (2H, —N$^+$—CH$_2$—), 5.9–6.4d (2H, =CH$_2$), 6.1dd (1H, =CH), 7.5, 7.6d/8.8s (1H, each C$_3$N$_2$H$_3$).

$^{13}$C N.M.R. (300 MHz, D$_2$0): 6=125.2 (CH=CH$_2$), 130.2 (CH=CH$_2$), 138.0 (N$^+$—CH$_2$), 134.5 (N—CH$_2$), 67.5 (CH$_2$O—C(=O)), 50.2 (CH—N), 52.3 (CH—N~), 49.2 (CH$_2$—C—SO$_3$), 31.30–28.0 (CHrC—O—, CH$_2$—C≡C—).

IR (KBr pellet): selected bands: 2920, 2850 cm$^1$ (C—H stretch), 1500,1600 cm$^1$ (C=C ring stretch), 1162 cm$^{-1}$ (S=O stretch), 1715 cm$^{-1}$ (C=O stretch), 1120 cm$^{-1}$ (C—C—O), 1216 cm$^1$ (C—(C=O)—C stretch).

Elemental Analysis: C$_{20}$1l$_{35}$N$_2$O$_6$S

| Calculated | C 56.68% | H 8.12% | N 6.49% | O 22.27% | S 6.44% |
| Experimental | C 56.69% | H 8.10% | N 6.34% | O 22.35% | S 6.52% |

Example 2

Synthesis of Zwitterionic Copolymerizable Surfactant Benzimidazole Based (ABIPSA)

The synthesis of ABIPSA can be carried out in accordance with the general synthesis scheme shown in FIG. 6A.

Firstly, 11-bromoundecan-1-ol, benzimidazole and sodium hydroxide solution in suitable molar ratios, for example 0.1 mol:0.08 mol:0.1 mol, respectively, can be dissolved in a suitable amount of solvent, e.g. ethanol, and refluxed for several hours. Upon cooling to room temperature, the precipitate thus formed is filtered and the solvent evaporated. After evaporating off the solvent, the filter residue is dissolved in another suitable organic solvent such as ether, and is washed with water and left to dry overnight in the presence of magnesium sulfate. A solid product is obtained after the evaporation of the solvent. The solid product is dried to a constant weight in vacuum.

The synthesis of 3-((11-hydroxyundecyl)-benzimidazolyl) propyl sulfonate (HUBIPS) can be carried out as follows. To a magnetically stirred solution of 11-hydroxyundecylbenzimidazole in dried acetonitrile, prepared for example by dissolving 0.1 mol in 200 ml of acetonitrile, 1,3 propane-sultone is added dropwise over a suitable period of time. A suitable, e.g. stoichiometric, amount of 1,3 propane-sultone can be added. The solution is refluxed for one day under nitrogen atmosphere. The product will precipitate out from the reaction mixture. The precipitate can then be filtered off and dried in a vacuum oven for one day at ambient temperature.

Subsequently, the synthesis of 3-((11-acryloyloxyundecyl)-benzimidazolyl) propyl sulfonate (ABIPSA) may be carried out as follows. A suitable, for example stoichiometric, quantity of acryloyl chloride is slowly added to a magnetically stirred solution of 3-((11-hydroxyundecyl)-benzimidazolyl) propyl sulfonate in dried acetonitrile at 0° C. purged with $N_2$ gas. The mixture is further reacted at room temperature for an extended period of time, e.g. 3 days. The mixture is filtered and the excess acryloyl chloride and acetonitrile are removed in a rotary evaporator. The filter residue is dissolved in a solvent such as distilled chloroform, washed twice with saturated sodium bicarbonate solution followed by saturated brine and left to dry overnight in the presence of magnesium sulfate. The pure product of 3-((11-acryloyloxyundecyl)-benzimidazolyl) propyl sulfonate can be obtained by re-precipitating the crude product in anhydrous ether, and then filtering out the precipitate, which is then dried in a vacuum oven.

Surfactants Having Saturated Ring Systems

A general synthesis route for surfactant compounds of the present invention having a monocyclic or bicyclic saturated ring system is shown in FIG. 6b. This synthesis route has been applied in the following examples to demonstrate how specific examples of these surfactant compounds are made.

Example 3

Synthesis of the Anionic Surfactant Compound 3-((11-acryloyoxyundecyl)-piperazinyl) propyl sulfonate (AUPSA)

In the first step, the following reaction was carried out:

In carrying out the reaction, piperazine was pre-dissolved in distilled ethanol at 70° C. At 70° C., NaOH aqueous solution was added dropwise to the reaction mixture. This mixture was then heated up to 77° C. At 77° C., HO—$(CH_2)_{11}$,—Br in EtOH solution was added dropwise to the reaction mixture. This reaction was continuously heated at 77° C. for another 24 hrs. The solution was then cooled to room temperature before it was subjected to drying using a rotary evaporator. The solid product thus obtained was washed with water and diethyl ether.

Subsequently, the sulfo-alkylation using a sultone was carried out according to the following reaction:

HO—$(CH_2)_{11}$, —$N(CH_2CH_2)_2NH$ was predissolved in dried acetonitrile at 80° C. At 80° C., propane sultone was added dropwise to the reaction mixture. The reaction was left overnight with $N_2$ bubbling. The white solid product thus obtained was filtered while the solution was hot. It was washed with hot acetonitrile and $CHCl_3$. The product was then left to dry overnight in a vacuum oven.

Thereafter, sodium hydroxide was added to the sulfonated intermediate to form a sodium sulfonate salt. HO—$(CH_2)_{11}$—$N(CH_2CH_2)_2N$—$(CH_2)_3$—$SO_3H$ was dissolved in MeOH/$H_2O$ at mild heat. To a clear solution, NaOH solution was added and stirred for about 1 hr. The solution was dried with a rotary evaporator and vacuum oven.

In the final step, an acroylyl chloride was added to yield AUPSA.

HO—$(CH_2)_{11}$—$N(CH_2CH_2)_2N$—$(CH_2)_3$—$SO_3Na$ was suspended in dried acetonitrile and the solution was cooled to 0° C. using an ice bath. With the $N_2$ bubbling, acryloyl chloride was then added dropwise to the reaction mixture. The reaction was continued for 4 days. The product thus obtained was centrifuged and washed with an excess of acetonitrile. The product obtained was protonated due to the presence of HCl:

Example 4

Synthesis of Copolymerizable Surfactant Containing an Imidazoline Ring System The synthesis of the above can be carried out in accordance with the general synthesis scheme shown in FIG. 6B.

Imidazoline (available from Jiangsu Feixiang Chemical Co. Ltd., for example) may be pre-dissolved in distilled ethanol at an elevated temperature, e.g. at about 70° C. Then, NaOH aqueous solution is added dropwise to the mixture. This mixture is heated to a suitable reaction temperature and HO—$(CH_2)_{11}$,—Br in EtOH solution is added dropwise to form the reaction mixture. The reaction can be maintained at the reaction temperature for an extended period of time, e.g. 24 hrs. After the reaction, the solution is then cooled to room temperature before it is dried using a rotary evaporator. The solid product that is obtained may be washed with water and an organic solvent such as diethyl ether.

Subsequently, sulfo-alkylation of the product obtained from the previous step using a sultone can be carried out as follows.

The product from the first step can be pre-dissolved in dried acetonitrile and the mixture is further heated to temperatures of, for example, up to about 80° C. Propane sultone is added dropwise to the reaction mixture and left overnight, accompanied by the bubbling of $N_2$. The white solid product can be filtered while the solution is hot. Then, the residue is washed with hot acetonitrile and $CHCl_3$. The product may be left overnight to dry in a vacuum oven.

Thereafter, sodium hydroxide can be added to the sulfonated intermediate as follows. The sulfonated intermediate is first dissolved in MeOH/$H_2O$ at mild heat to form a clear solution, to which NaOH solution is added. The mixture is stirred for about 1 hr and then dried with a rotary evaporator and vacuum oven.

Then, an acroylyl chloride may be added. For this purpose, the intermediate from the previous step is suspended in dried acetonitrile and the solution is cooled to 0° C. using an ice bath. With the $N_2$ bubbling, acryloyl chloride is added dropwise to the reaction mixture. The reaction can be continued for an extended period of time, e.g. 4 days. The surfactant product is centrifuged and washed with an excess of acetonitrile.

Example 5

Synthesis and Ionic Conductivity Tests of Ion-conducting Membranes Using the Copolymerizable Surfactant Compounds AIPSA and AUPSA Using the copolymerizable surfactants synthesized in Examples 1 and 2, bicontinuous precursor microemulsions were prepared in order to evaluate their protonic conductivities. Microemulsions of differing compositions as tabulated in FIG. 4 were first prepared. The microemulsions were impregnated onto a glass-fiber sheet, before applying a UV photo-initiator, 2,2 dimethoxy-2-phenyl acetophenone (DMPA), to initiate polymerization. After about 8 hours of polymerization, structurally stable membrane sheets were obtained. Thereafter, the sheets were treated with 0.5M $H_2SO_4$. The membranes were then tested with a fuel cell using a 0.4 mg/cm$^2$ loading electrode.

The final conductivities of the polymeric materials were determined using an EG&G model 273 potentiostats/galvanostat using system software. Cell impedances were measured in the frequency range of 1 Hz to 100 kHz by connecting the EG&G 273 to a EG&G model 5210 lock-in amplifier, and using an ac modulation voltage of ±10 mV (the conductivities were evaluated by extrapolating the impedance arc to intercept the real axis from Cole-Cole plots).

Figure 4:
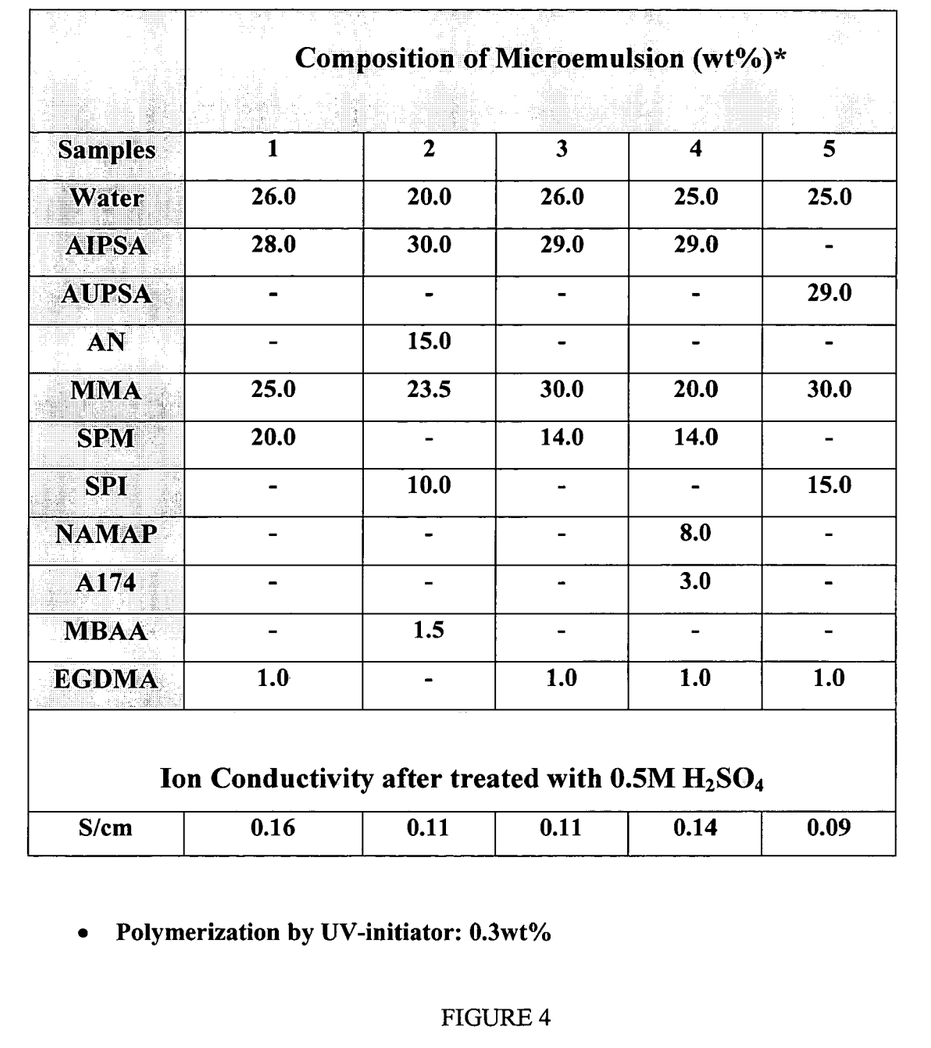
FIG. 4 shows the compositions and ion conductivities of 5 membranes formed from polymers embodying the present invention.

FIG. 4 show tables which give the composition and protonic conductivity of the 5 membranes, each of which were synthesized by methods embodying the present invention from bicontinuous microemulsions consisting of polymerizable surfactants:

AIPSA [$SO_3$–$(CH_2)_m$<sup>+</sup>NCHCHCHN$(CH_2)_n$ COOCH=$CH_2$], and

AUPSA [$SO_3$–$(CH_2)_m$N$(CH_2CH_2)$N$(CH_2)_n$V], using monomers such as acrylonitrile (AN) and methyl methacrylate (MMA), N-acryloyl-N'-methylpiperazine (NAMAP), 3-sulphopropylmethacrylic acid ester (SPM) Bis-3-sulphopropyl-itaconic acid ester (SPI), and using N'N methylene bis-acrylamide (MBBA) or ethylene glycol dimethacrylate (EGDMA) or γ-methacryloxypropyltrimethoxysilane (A174) as a crosslinker.

It can be seen that the ionic conductivities of the 5 membranes listed therein are comparable or better than those of currently available membranes, which are in the range of 0.01 to 0.1 S/cm.

Figure 5:
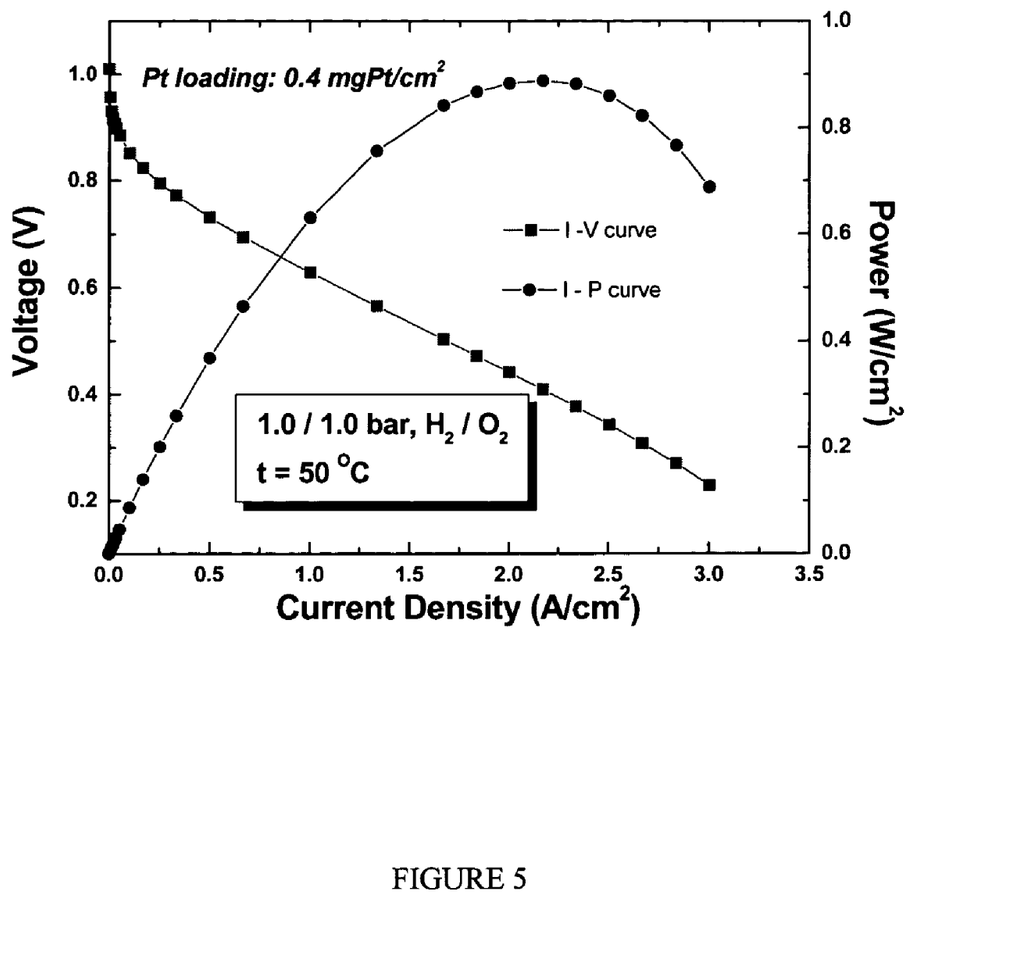
FIG. 5 shows a typical Voltage vs. Current density and Power Density vs. Current Density graphs for a membrane in Example 4 of FIG. 4.

In order to carry out further evaluation of the characteristics of the synthesized membranes, the Voltage vs. Current Density and Power Density vs. Current Density graphs were obtained for membrane 4 as shown in FIG. 5.

Example 6

Synthesis of Ion-conducting Membranes Using the Copolymerizable Surfactant Compound AIPSA AIPSA was prepared in accordance with Example 1. Methyl methacrylate (MMA) was obtained from Aldrich and purified under reduced pressure prior to use. Distilled deionized water was used in all examples.

Figure 7:
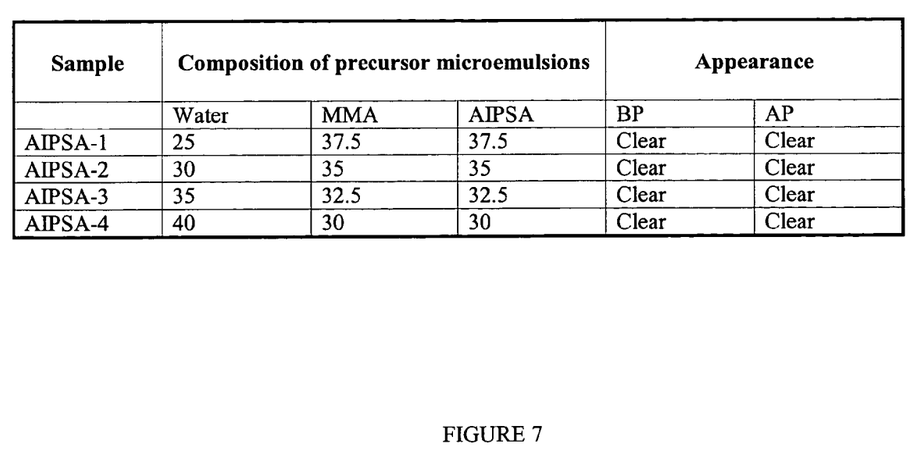
FIG. 7 shows different compositions of AIPSA containing precursor microemulsions which were used for the preparation of membranes of the invention. In each of the compositions shown in FIG. 7, an amount of 5 wt % cross-linker ethylene glycol dimethacrylate (EGDMA) was added on the basis of the total weight of monomers used in each system; ammonium persulfate/N,N,N',N',-tetramethylethylenediamine (APS/TMEDA) (20 mM/20 mM) was added on the basis of the aqueous content used in the system. The abbreviation "BP" denotes "Before Polymerization" and the abbreviation "AP" denotes "After Polymerization".

Microemulsion mixtures having the compositions indicated in FIG. 7 were prepared by introducing corresponding ratios of AIPSA, MMA and water into a test tube. 5% EGDMA cross-linker based on the total weight of all reactive monomers was added to each microemulsion sample. The microemulsion samples were vortex-mixed and allowed to equilibrate in a temperature controlled environment at 23° C. Subsequently, the samples were ultrasonicated for 20 s to eliminate bubbles formed during mixing. Polymerization of the microemulsion samples was initiated with a redox initiator using equimolar ammonium persulfate/N,N,N',N',-tetramethylethylenediamine (APS/TMEDA) of 20 mM/20 mM based on water content and carried out in a Rayonet photoreactor chamber at about 35° C. for 8 hours to obtain polymerized microemulsion samples. Pre-polymerization of the microemulsion occurs within 15 minutes when redox initiators are used. If UV initiators are used, after adding and mixing of the UV initiator, the microemulsion precursor is poured immediately onto the respective glass plates and thereafter the system is subjected to polymerization in a photoreactor chamber for 8 hrs.

Two 20 cm by 20 cm glass plates were washed and coated with a small amount of silicon oil. The silicon oil allows the membrane to be easily detached from the glass plates later on. The semi-polymerized microemulsion samples were spread between the two glass plates. Then, the glass plates were placed in the Rayonet chamber and the microemulsion samples were subjected to further polymerization at about 35° C. for 24 hrs.

The membrane samples thus formed were then placed in 0.5M $H_2SO_4$ for 24 hrs at 70° C. and subsequently rinsed and stored in Millipore water for 24 hrs prior to use.

Preliminary lifetime tests show that the performance of cells manufactured using the above prepared membranes remains stable after a prolonged period of operation of the cell (about 2500 hours) at normal temperature and pressure.

In summary, the present invention provides novel surfactants and processes for producing them, as well as ion conducting membranes which incorporate these surfactants, and processes for producing the membranes. These membranes display significant advantages over conventional membranes, including increased ionic conductivity and reduced cost of production.

What is claimed is:

1. A compound having the formula (1):

$$^-O_3S—R_1—V_1—R_2—V_2$$

wherein $R_1$ is a hydrocarbon radical comprising 1 to 10 main chain carbon atoms, wherein hydrogen atoms bonded to the main chain carbon atoms are independently substituted or not substituted;

$R_2$ is a hydrocarbon radical comprising 6 to 20 main chain carbon atoms, wherein hydrogen atoms bonded to the main chain carbon atoms are independently substituted or not substituted;

$V_1$ is a saturated or unsaturated, monocyclic or bicyclic ring system comprising 5 to 9 ring atoms, wherein at least 2 ring atoms are nitrogen atoms, said nitrogen atoms being comprised in the same cycle;

$V_2$ has the formula (II)

$$—O—\overset{O}{\underset{\|}{C}}—\overset{R_3}{\underset{|}{C}}=C\overset{R_4}{\underset{R_5}{{}^{/}_{\backslash}}}$$

wherein $R_3$, $R_4$, and $R_5$ are independently selected from the group consisting of H and a $C_1$–$C_4$ alkyl group, wherein each $C_1$–$C_4$ alkyl group is independently substituted or not substituted.

2. The compound according to claim 1, wherein the ring system of $V_1$ is an unsaturated, 5 or 6 membered monocyclic ring system.

3. The compound according to claim 2, wherein the unsaturated or aromatic, 5 or 6 membered monocyclic ring system is selected from the group consisting of imidazole, pyrazole, 1,2,4-triazole, tetrazole and pyrazine.

4. The compound according to claim 1, wherein the ring system of $V_1$ is a saturated, 5 or 6 membered monocyclic ring system.

5. The compound according to claim 4, wherein the saturated, 5 or 6 membered monocyclic ring system is selected from the group consisting of piperazine and imidazoline.

6. The compound according to claim 1, wherein the bicyclic ring system of $V_1$ is an unsaturated, 9 member bicyclic ring system.

7. The compounds according to claim 6, wherein the unsaturated, 9 member bicyclic ring system is selected from the group consisting of benzimidazole, purine and indazole.

8. The compound according to claim 1, having the formula (II):

$$^-O_3S—(CH_2)_m—\overset{+}{N}\underset{\diagdown\!\diagup}{\diagup\!\diagdown}N—(CH_2)_n—O—\overset{O}{\underset{\|}{C}}—\overset{}{\underset{H}{C}}=CH_2$$

wherein $1 \leq m \leq 10$ and $6 \leq n \leq 20$.

9. The compound according to claim 1, having the structural formula (IV):

$$XSO_3(CH_2)_m N(CH_2CH_2)N(CH_2)_n V$$

where $6 \leq n \leq 20$, $1 \leq m \leq 10$, X=$Na^+$, $Li^+$, $NH_4^+$, and V is (methyl)acrylate or another copolymerizable unsaturated group.

10. An ion conducting membrane comprising a copolymer, wherein said copolymer comprises a monomer having the formula (I):

$$^-O_3S—R_1—V_1—R_2—V_2$$

wherein $R_1$ is a hydrocarbon radical comprising 1 to 10 main chain carbon atoms, wherein hydrogen atoms bonded to the main chain carbon atoms are independently substituted or not substituted;

$R_2$ is a hydrocarbon radical comprising 6 to 20 main chain carbon atoms, wherein hydrogen atoms bonded to the main chain carbon atoms are independently substituted or not substituted;

$V_1$ is a saturated or unsaturated, monocyclic or bicyclic ring system comprising 5 to 9 ring atoms, wherein at least 2 ring atoms are nitrogen atoms, said nitrogen atoms being comprised in the same cycle;

$V_2$ has the formula (II):

$$—O—\overset{O}{\underset{\|}{C}}—\overset{R_3}{\underset{|}{C}}=C\overset{R_4}{\underset{R_5}{{}^{/}_{\backslash}}}$$

wherein $R_3$, $R_4$, and $R_5$ are independently selected from the group consisting of H and a $C_1$–$C_4$ alkyl group, wherein each $C_1$–$C_4$ alkyl group is independently substituted or not substituted.

11. A process for the preparation of a compound having the formula (I):

$$^-O_3S—R_1—V_1—R_2—V_2$$

wherein $R_1$ is a hydrocarbon radical comprising 1 to 10 main chain carbon atoms, wherein hydrogen atoms bonded to the main chain carbon atoms are independently substituted or not substituted;

$R_2$ is a hydrocarbon radical comprising 6 to 20 main chain carbon atoms wherein hydrogen atoms bonded to the main chain carbon atoms are independently substituted or not substituted;

$V_1$ is a saturated or unsaturated, monocyclic or bicyclic ring system comprising 5 to 9 ring atoms, wherein at least 2 ring atoms are nitrogen atoms, said nitrogen atoms being comprised in the same cycle;

$V_2$ has the formula (II):

wherein $R_3$, $R_4$, and $R_5$ are independently selected from the group consisting of H and a $C_1$–$C_4$ alkyl group, wherein each $C_1$–$C_4$ alkyl group is independently substituted or not substituted, said process comprising:

a) reacting a compound having a saturated or unsaturated, monocyclic or bicyclic ring system comprising 5 to 9 ring atoms, wherein at least 2 ring atoms are nitrogen atoms, said nitrogen atoms being comprised in the same cycle, with an alcohol having the structure:

wherein

X' is halogen, and $R_2$ is a hydrocarbon radical comprising 6 to 20 main chain carbon atoms, wherein hydrogen atoms bonded to the main chain carbon atoms are independently substituted or not substituted;

b) reacting the product obtained from a) with a sultone; and c) reacting the product obtained from b) with a compound having the formula (IIa):

wherein

X is a halogen; and $R_3$, $R_4$ and $R_5$ are independently selected from the group consisting of H and a $C_1$–$C_4$ alkyl, wherein each $C_1$–$C_4$ alkyl group is independently substituted or not substituted.

12. A process for producing an ion conducting membrane, comprising copolymerizing at least one copolymerizable surfactant with a copolymerizable monomer in a bicontinuous microemulsion polymerization mixture, said mixture comprising:

i) about 15% to 50% by weight water;

ii) about 10% to 50% by weight of at least one copolymerizable surfactant having the formula (I):

wherein $R_1$ is a hydrocarbon radical comprising 1 to 10 main chain carbon atoms, wherein hydrogen atoms bonded to the main chain carbon atoms are independently substituted or not substituted;

$R_2$ is a hydrocarbon radical comprising 6 to 20 main chain carbon atoms, wherein hydrogen atoms bonded to the main chain carbon atoms are independently substituted or not substituted;

$V_1$ is a saturated or unsaturated, monocyclic or bicyclic ring system comprising 5 to 9 ring atoms, wherein at least 2 ring atoms are nitrogen atoms, said nitrogen atoms being comprised is the same cycle;

$V_2$ has the formula (II):

wherein $R_3$, $R_4$, and $R_5$ are independently selected from the group consisting of H and a $C_1$–$C_4$ alkyl group, wherein each $C_1$–$C_4$ alkyl group is independently substituted or not substituted, and iii) about 5% to 40% by weight of at least one copolymerizable monomer;

wherein said weight percents are based on the total weight of the microemulsion.

* * * * *